United States Patent [19]

Peterson

[11] 4,334,997
[45] Jun. 15, 1982

[54] ANAEROBIC DIGESTER TECHNOLOGY

[76] Inventor: Richard E. Peterson, 382 Pierce Ave., St. Paul, Minn. 55104

[21] Appl. No.: 231,959

[22] Filed: Feb. 6, 1981

[51] Int. Cl.³ .............................................. C02F 3/28
[52] U.S. Cl. .................................... 210/603; 210/608; 210/95; 210/180; 210/532.2
[58] Field of Search ................. 210/603, 608, 613, 95, 210/94, 180, 532.2; 48/197 A; 435/167, 801

[56] References Cited

U.S. PATENT DOCUMENTS

| | | | |
|---|---|---|---|
| 1,120,351 | 12/1914 | Weston | 210/532.2 |
| 1,314,955 | 9/1919 | Flicker | 210/603 |
| 2,069,058 | 1/1937 | Davis | 210/532.2 |
| 2,078,260 | 4/1937 | Mallory | 210/532.2 |
| 2,188,847 | 1/1940 | Streander | 210/603 |
| 3,056,749 | 10/1962 | Griffith | 210/608 |
| 3,904,524 | 9/1975 | Pelton | 210/532.2 |
| 4,100,023 | 7/1978 | McDonald | 435/167 |
| 4,211,647 | 7/1980 | Friedman | 210/603 |

FOREIGN PATENT DOCUMENTS

| | | | |
|---|---|---|---|
| 2811392 | 9/1979 | Fed. Rep. of Germany | 210/532.2 |
| 547052 | 8/1956 | Italy | 210/532.2 |
| 2037731 | 6/1980 | United Kingdom | 210/180 |

OTHER PUBLICATIONS

L. John Fry, Practical Building of Methane Power Plants for Rural Energy Independence, 1974, pp. 22 and 23.
Al Rutan, The Do's & Dont's of Methane, Gas Production for Self Sufficiency, 1979, 1980, pp. 83, 84B, 84G, 84H and 85.

Primary Examiner—Ernest G. Therkorn
Attorney, Agent, or Firm—Anthony G. Eggink

[57] ABSTRACT

The anaerobic, displacement-type digester is for the biological production of methane gas. The process involves the anaerobic digestion of solid waste and water or a sewage slurry to produce a methane-rich gas, which can be utilized for its energy value. The digester includes a tank-type enclosure comprising an input end, a digesting chamber and an output end. At the output end a sealable output chamber is provided which can separate the output end from the digesting chamber. The output chamber is comprised of a lower partition and an upper partition, which allows the output chamber to be sealed from the digesting chamber. As waste material is introduced at the input end of the digester, a slurry is formed. The upper stratum of material or scum must periodically be removed from the slurry to provide space for additionally introduced waste into the digester and to optimize the anaerobic digestion process. An upper stratum displacement means is provided at the digesting chamber of the digester. The displacement means removes the upper stratum of material over the lower partition into the output chamber. When the level of material in the output chamber rises to emerge the bottom of the upper partition a seal is formed between the output chamber and the digesting chamber. This seal allows the scum material to be removed from the output chamber without excessive loss of methane gas from nor introduction of air into the digesting chamber of the digester.

11 Claims, 4 Drawing Figures

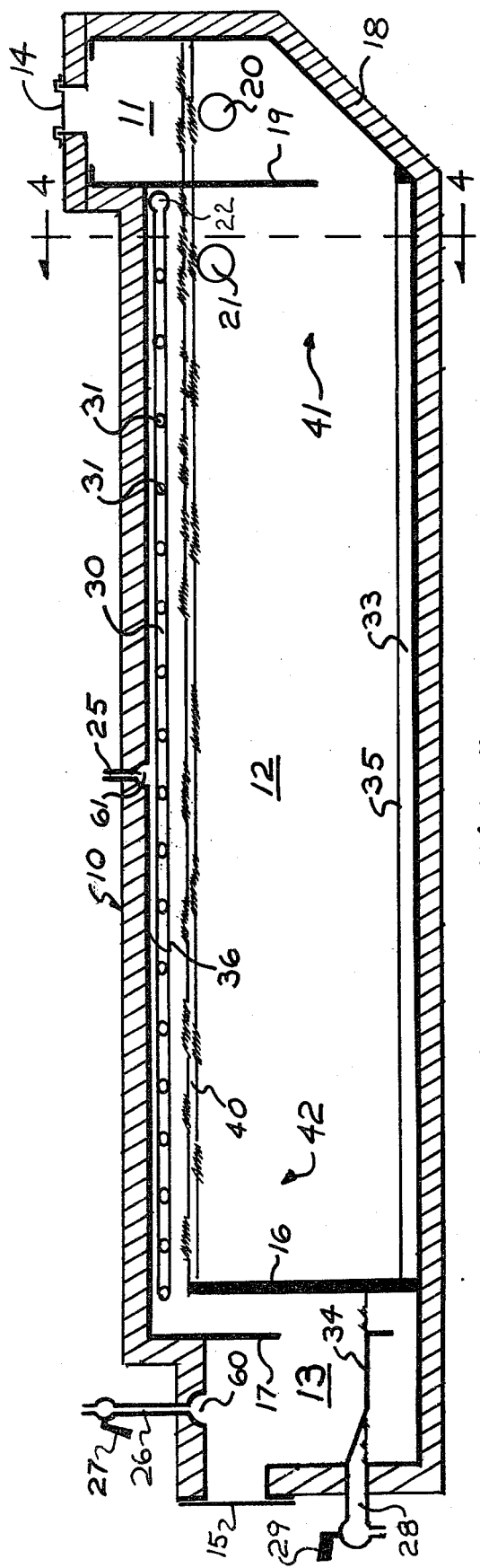
FIG. 1
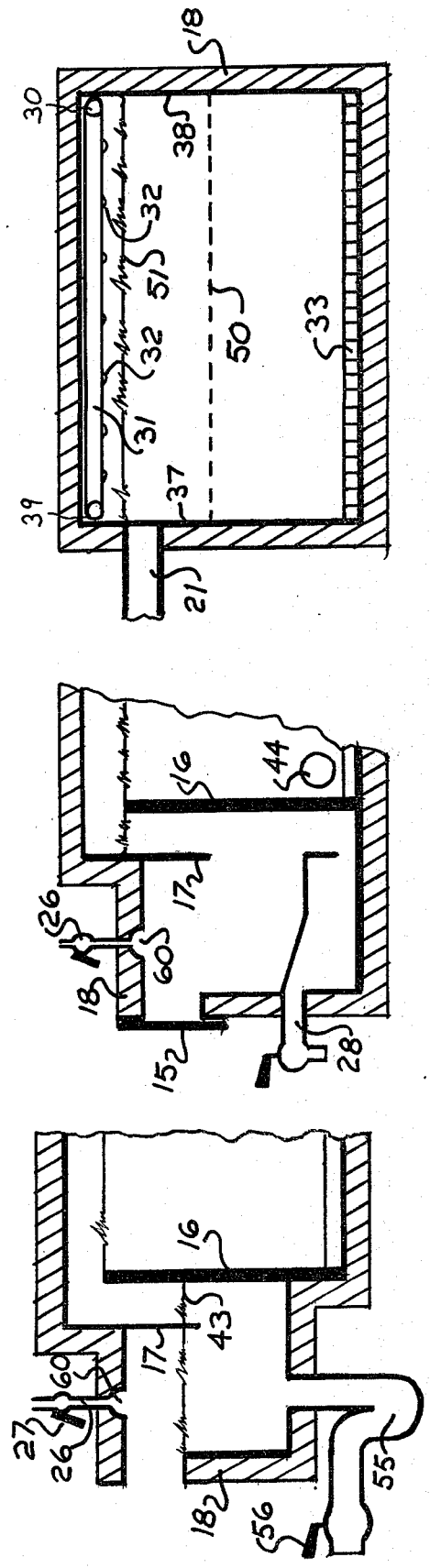
FIG. 4
FIG. 3
FIG. 2

ANAEROBIC DIGESTER TECHNOLOGY

This invention relates to an anaerobic, displacement digester for the production of methane-rich gas from the biological digestion of solid waste and water or a sewage slurry. Particularly, this invention relates to a removal system for an anaerobic digester to allow predetermined components to be removed from the digester without excessive loss of methane gas from nor introduction of air into the digesting chamber of the digester.

Anaerobic digesters are containers or tanks in which a specific biological process is utilized to convert organic waste materials to a methane rich gas and other products. This type of methane power plant process has become particularly known for its ability to convert waste materials common to residential, commercial, and agricultural settings to an energy source, methane.

The anaerobic digesting process is one which involves a series of reacting steps by bacteria which function only in an anaerobic or oxygen free environment. The anaerobic bacteria initially digests the raw waste material into an intermediate state which subsequently is converted by another anaerobic microorganism into methane.

Although a number of anaerobic digester process designs are known, the displacement type has proven advantageous in many respects. It offers continuous operation with minimal outside interaction. The displacement digester is generally an enclosed, air-tight receptacle having an input for receiving waste materials, a holding or digesting chamber where this waste is transformed by means of the anaerobic microorganisms and where the resultant materials are allowed to stratisfy, and an output end for the removal of predetermined components of the stratified materials.

Although the methane rich gas produced in the digesting chamber is continually removed from a location at the top of the chamber, not all of the waste materials that enter are organic or digestible. Thus, the continual ingress of waste which displaces the digesting materials from the input end towards the output end of the digester ultimately causes a buildup of inorganic, indigestible and other transformed, non-gaseous materials. This buildup increasingly reduces the efficiency and operation of the digester.

One primary difficulty that is encountered in displacement digesters is the buildup of lower density materials or scum in the upper stratum of the digesting chamber. While the removal of higher density transformed materials can be effectuated by means of a pipe at the bottom portion of the digesting chamber toward the output end, the removal of scum buildup has generally required the shutting down of the digesting process or has involved means which allowed the entry of air into the digesting chamber and thereby destroying the anaerobic environment in the chamber and, in addition loss of methane gas.

It is, therefore, the object of this invention to provide a removal system for transferring the upper stratum of materials from the digesting chamber and out of the digester receptacle with minimal loss of methane gas, minimal entry of air, and, thus, minimal disturbance on the digesting process in the digesting chamber.

In summary, this invention provides a removal system for transferring predetermined components from a holding chamber of an enclosed receptacle such as an anaerobic digester. The removal system allows the transfer of these components from the holding chamber with minimal entry of gaseous matter into or exit of gaseous matter from the holding chamber during the removal process of the predetermined components. The removal system of the invention comprises:

(a) an output chamber for sealing the output end of the digester from the holding chamber, the output chamber having a lower partition extending upward from the bottom and concongruous with the opposing side walls of the receptacle and having a horizontal edge spacially removed from the top of the receptacle, and an upper partition disposed generally parallel to and towards the output end from the lower partition, the upper partition extending downward from the top of the receptacle congruous with the opposing side walls and having a lower edge spacially removed from the bottom of the receptacle, the lower edge of the upper partition being spacially downward from the horizontal edge of the lower partition, and (b) an upper stratum displacement means for transporting the upper strata of matter in the holding chamber from generally the input end of the receptacle over the horizontal edge of the lower partition into the output chamber, whereby a seal is formed by the displaced matter upon the level of the displaced matter reaching at least the lower edge of the upper partition so that a portion of the displaced matter can be removed from the output chamber of the receptacle with minimal disturbance to the remaining matter in the holding chamber.

Additionally provided by this invention is an upper stratum displacement means consisting of a plurality of fluid spray nozzles, additional special features and advantageous structures and functions of the output chamber, as well as a method for removing predetermined components from the holding chamber of an enclosed receptacle with minimal interference on the remaining matter in the holding chamber.

These and other benefits of this invention will become clear from the following description by reference to the drawings, wherein:

FIG. 1 is a lateral plan view of a typical displacement type anaerobic digester having the removal system of this invention;

FIG. 2 is a lateral plan view of an embodiment of the output chamber of the invention;

FIG. 3 is a lateral plan view of another embodiment of the output chamber of the invention; and, FIG. 4 is a schematic, cross section of the displacement digester taken on lines 4—4 of FIG. 1.

Referring to FIG. 1, a typical displacement type anaerobic digester 10 is illustrated. The digester or methane power plant is an enclosable receptacle having an input end 11, a holding or digesting chamber 12, and an output end 13. The digester 10 is shown as a generally rectangular structure having an interior top area 36, opposing side walls 37 and 38, and an interior bottom area 35. However, digesters need not have a rectangularly shaped structure, and curvilinear tank shaped structures have also been found to function adequately.

The digester shown in FIG. 1 is an enclosable receptacle for receiving waste materials. The closable aspect of the digester is important in that the biological process which converts the waste material into a methane rich gas and a nitrogen rich effluent is anaerobic in nature. Thus, the microorganisms or bacteria which transform the waste materials into these usable end products, only function in an environment which is free from air or oxygen. This requirement, and the fact that the displacement type process is continuous in nature, are important to note when considering the benefits of this invention.

Digester 10 is usefull for residential, commercial and agricultural purposes. However, the nature of the waste material put into the digester for conversion is important to its operation. For example, inlet pipe 20 which enters input end 11 can carry waste from a garbage disposal. Inlet pipe 21 which enters into the digesting chamber directly, on the opposite side of baffle plate 19, can carry waste from a toilet. Baffle plate 19 separates input chamber 11 from the digesting chamber 12. A removable door or entry port 14 provides access into the input chamber for removal of debris and the feeding and mixing of wastes. This door or port cover 14 is shown as a snap-on device made of a plastic or similar material. Although inlet pipes 20 and 21 were described above as carrying typical household wastes, these entry pipes carry suitable agricultural wastes, such as animal manures, plant by-products, cellulose materials, etc., as the individual requirements dictate.

Typically, oxygen or air containing wastes are brought directly into the input chamber 11 by means of pipe 20, for example, sothat the air or oxygen does not directly enter the digesting chamber 12. Alternatively, a vent means, not shown, connects the top portion of the input chamber to the atmosphere to allow the escape of the air or oxygen from the input chamber.

After the wastes enter the input chamber 11, they mix and compact and ultimately enter the digesting chamber 12 by sliding beneath baffle plate 19. Upon entry into the holding or mixing chamber 12, the waste or slurry material proceeds through an acid phase. This phase typically takes place in the first quadrant or one-third of the digesting chamber and which is designated by 41 in FIG. 1. The acid phase 41 constitutes a step in the biological transformation of the raw organic waste materials, and which step produces the transformed material upon which the methane producing bacteria or microorganism feed. This latter process taking place in the portion of the digesting chamber desigby numeral 42 in FIG. 1. Although some carbon dioxide is produced by the microorganisms in acid phase 41, the greater proportion of gas produced in the digesting chamber is methane. It should be pointed out that the anaerobic bacteria or microorganisms are generally latent in the waste materials entering the digester, and which multiply in the anaerobic environment with time.

As described above, a methane rich gas is formed by the biological process in the digesting chamber 12. The gas is removed from that chamber through a gas output pipe 25 which is connected to a gas dome configuration 61 at the upper surface 36 of the digesting chamber. The resultant gas is transported through gas output pipe 25 to a holding tank or to a scrubber apperatus to refine the gas before usage.

The foregoing description of the digester operation assumes complete conversion of the waste material into a methane rich gas, and a nitrogen rich effluent. And, ideally, the entering waste materials comprise a carbon/nitrogen ratio of 30 to 1, while the digesting chamber temperature is kept at 90° F. by a heating means 33 located at the bottom of the digesting chamber. However, some waste materials, such as inorganic matter, do not undergo digestion. Additionally, the nature of the biological process results in the production in the digesting chamber 12 an upper stratum or scum 40 which rises to the top surface of the digesting slurry. The formation of scum at the upper stratum presents, perhaps, one of the greatest burdens to the anaerobic digester technology, and it is this problem with which this invention deals.

Scum buildup 40 in the digesting chamber inhibits the biological process, and thus the production of methane rich gas. It also has a tendency to clog the gas output pipe 25, and also interferes with input pipes 20 and 21, and the slurry removal pipe 44. The scum 40 is generally comprised of lower density materials, such as animal hair, straw, feathers or inorganic matter which floats at the upper stratum of the digesting slurry.

The upper stratum removal system has an output chamber at output end 13 of the digester. The output chamber is spacially defined by a lower partition 16 which extends generally upward from the interior bottom surface 35, and which is congruous with or connected to opposing wall areas 37 and 38. A generally horizontal or upper edge 51, as shown in FIG. 4, is spacially removed from the upper surface or interior top area 36 of the digesting chamber 12. Thus, the lower partition 16 forms a spill dam for upper stratum material in the digesting chamber.

An upper partition 17 disposed generally parallel to and spacially towards the output end 13 relative to lower partition 16 is another element defining the output chamber. The upper partition 17 is congruous with the opposing side walls 37 and 38, and has a lower edge 50, which is spacially removed from the interior bottom of the output end 13 as shown in FIG. 4. The output chamber additionally has an entry door or port opening 15, a gas output pipe 26 extending from dome 60, and an effluent output pipe 28. The output chamber can be equipped with a baffle plate 34 or alternatively with a trapped effluent pipe 55 as shown in FIG. 2.

An upper stratum displacement means for effectuating the transport of scum 40 over the lower partition 16 is illustrated in FIGS. 1 and 4. Although mechanical drag-style apparatus have been utilized for this purpose, the displacement means shown here consists of longitudinally extending fluid pipes 30 and 39, which extend generally from baffle plate 19 to lower partition 16. A fluid inlet pipe 22 provides an oxygen free fluid source to pipes 30 and 39 from the outside of the digester. Latitudinally extending fluid pipes 31 are operatically connected to pipes 30 and 39, and protruding from the bottom surface of latitudinal pipes 31 are a plurality of fluid jets 32. The longitudinal and latitudinal pipes are fastened at generally the upper surface 36 of the digesting chamber and above the scum 40 level therein.

In operation, a fluid such as water, generally free of $O_2$, is sent through fluid inlet 22 and ultimately is sprayed through jets or nozzles 32 to transport scum 40 over lower partition 16 into the output chamber. The jets are disposed downward from pipes 31 and preferable tilt toward the output end of the digester. Means to sequentially operate the latitudinal pipes 31 from generally the input end to the output end of the digester aids the transport of scum 40 out of the digesting chamber 12.

As the predetermined components, scum 40 and effluent are spilled into the output chamber the level of the material rises to fill that chamber. Ultimately, as shown in FIG. 3, the chamber is filled, and the material disposed between lower partition 16 and upper partition 17 forms a seal between the output chamber and the digesting chamber 12 so that the components in the output chamber can safely be removed from the digester with minimal disturbance to the ongoing digesting process. As shown in FIG. 2, output chamber door 15 can be removed to provide access into the output end. The entry of air into digesting chamber is minimized by the seal fluid 43, and conversely, the escape of methane rich gas from the digesting chamber 12 into the output chamber is also minimized by seal fluid 43.

As discussed above, the digester or methane power plant 10 is useful in a variety of settings. Generally, the size of the digester depends upon the amount and type of waste that is desired to be digested and converted. It has been found that a digester having a capacity to hold and digest waste materials for a thirty day period is optimal for most settings. Thus, the waste materials that enter the input end of the digester displace in a general sense the materials that were placed therein thirty days prior. And, the process of input to acid phase conversion 41 and the resultant methane rich gas and nitrogen rich effluent at 42 becomes a thirty day cyclic event.

A digester 10 having fiberglass or fiberglass on plywood supporting sheets walls and other components, such as the baffle plates, partitions, etc., have been found economical and easy to assemble. The outside wall surfaces can also be insulated by urethane or other insulating materials sothat the 90° F. digester temperature can be maintained with minimal heat loss. Digester wall 18 indicates a typical fiberglass/insulation wall. And, a digester built in this fashion having general dimensions of a 16 ft. length, 3 ft. width and 2 ft. height provides adequate volume for a 30 day cycle for the typical user.

After initial start-up of the digester, waste materials compact, stratisfy, and are transformed as described above. After the level in the digesting or holding chamber 12 reaches the top of lower partition 16, additional input of waste causes scum 40 and effluent to spill over the upper horizontal edge 51 of partition 16 and into the output chamber. Initially the effluent fills the bottom of the output chamber as shown in FIG. 1, and the scum 40 floats on top of the effluent. Output chamber baffle 34 allows effluent to be removed because of the seal that it provides therein, and alternatively, as shown in FIG. 2, the trapped effluent output pipe 55 provides a similar seal. Valve means 29 for effluent output 28, and valve means 56 for output pipe 55 are utilized to remove the nitrogen rich effluent which can subsequently be utilized as a fertilizer.

The output chamber can also be provided by a viewing means, not shown, such as a clear plastic window, sothat the amount of scum 40 in the output chamber can be monitered. This scum, is the result of displacement and of the use of the upper stratum displacement means as previously described. Valve means 27 on gas output pipe is utilized to siphon the trapped gasses in the output chamber, and finally the scum 40 is removed from the output chamber through output door or port 15. Additionally, a water or fluid input pipe can be brought into the interior of the output chamber so that the proper fluid seal 43 is maintained during the scum removal process. In summary, this method of operation for an anaerobic, displacement type, methane digester or power plant allows the user of the digester to remove predetermined components from the digester tank with minimal disturbance on the biological process within the digesting chamber, and with minimal loss of the methane rich gas produced therein.

As many changes are possible to the embodiments of this invention utilizing the teachings of the invention, the descriptions above and the accompanying drawings should be interpreted in the illustrative and not in the limited sense.

That which is claimed is:

1. In an anaerobic digester having an input end for ingress of matter, a holding chamber for stratification and transformation of the matter, and an output end for removal of predetermined components of the stratified and transformed matter, said digester having an interior top area, opposing side wall areas and an interior bottom area, a removal system for said digester to provide means to transfer the predetermined components from said holding chamber to said output end with minimal disturbance on the matter in said holding chamber, said removal system comprising:

(a) an output chamber for sealing said output end from said holding chamber, said output chamber having a lower partition extending generally upward from said interior bottom area congruously with said opposing side wall areas and having a generally horizontal edge spacially removed from said interior top area, and an upper partition disposed generally parallel to and being essentially placed towards said output end relative to said lower partition, said upper partition extending generally downward from said interior top area congruously with said opposing side wall areas and having a lower edge spacially removed from said interior bottom area of said digester, and, (b) an upper stratum displacement means for transporting an upper stratum of matter from said holding chamber over said horizontal edge of said lower partition and into said output chamber by spraying fluid on the upper stratum, whereby a seal is formed between said output chamber and said holding chamber subsequent to the transfer of upper stratum matter from said holding chamber by said upper stratum displacement means as the level of the displaced matter reaches at least said lower edge of said upper partition to permit the removal of the displaced matter from said output chamber with minimal disturbance to the remaining matter in said holding chamber.

2. The anaerobic digester of claim 1, wherein the digester is an anaerobic, displacement digester for the biological production of a methane rich gas and a nitrogen rich effluent from an organic waste material slurry, and, wherein the predetermined components comprise the scum material at the upper stratum of the slurry and the nitrogen rich effluent.

3. The anaerobic digester of claim 2, wherein said output chamber additionally has scum removal means, effluent output means, gas output means, fluid input means, and viewing means.

4. The anaerobic digester of claims 1 or 2, wherein, said upper stratum displacement means comprises a plurality of activatable generally non-free-oxygen containing fluid jets disposed at said interior top area from generally said input end to generally said lower partition, whereby the spray of fluid from said jets displaces the upper stratum of matter over said horizontal edge of said lower partition into said output chamber.

5. The anaerobic digester of claim 1, wherein said upper stratum displacement means comprises a plurality of activatable water jets, said water jets disposed in a generally downward position tilting towards said output chamber, said water jets operatically connected to a plurality of latitudinally extending water pipes disposed spacially from said interior upper surface of said digester, said latitudinally extending water pipes operatically connected to at least one longitudinally extending water pipe, said longitudinally extending water pipe being operatically connected to a water source outside said digester.

6. The anaerobic digester of claim 5, wherein said latitudinally extending water pipes have means to sequentially be operatable from the input end to the lower partition area of said digester, whereby the activation of water flow from said outside water source through said longitudinally extending water pipes and through said downward facing, tilted toward said output chamber, water jets sequentially causes an upper stratum of matter within said holding chamber to be transferred by said displacement means from said input end area of said holding chamber over said lower partition and into said output chamber.

7. An anaerobic, displacement-type digester for the biological production of methane gas through the anaerobic bacteriological change of organic waste materials when placed therein, said digester having an input end for the introduction of waste materials, a digesting chamber for the stratification and biological transformation of waste materials, and an output end for primarily the removal of the upper stratum scum material which results from the activity in the digesting chamber, said digester having an interior top area, opposing side wall areas and an interior bottom area, said digester further having a removal system to transfer generally the upper stratum scum material from the digesting chamber with minimal disturbance on the anaerobic activity when taking place therein, said removal system comprising:
 (a) a sealable output chamber for sealing the output end from the digesting chamber, said output chamber having a lower partition extending generally upward from the interior bottom area congruously with the opposing side wall areas and having a generally horizontal edge spacially removed from the interior top area of said digester, and an upper partition disposed generally parallel to and being essentially placed towards the output end relative to said lower partition, said upper partition extending generally downward from the interior top area congruously with the opposing side wall areas and having a lower edge spacially removed from the interior bottom area of the digester, and,
 (b) an upper stratum displacement means for transporting upper stratum scum materials from the digesting chamber over said horizontal edge of said lower partition and into said output chamber by spraying fluid on the upper stratum, whereby the transfer of upper stratum scum materials by said displacement means produces a seal between the digesting chamber and said output chamber as the displaced materials reach at least said lower edge of said upper partition to permit the removal of the displaced materials from said output chamber with minimal disturbance on the anaerobic activity when taking place within the digesting chamber of said digester.

8. The anaerobic, displacement-type digester of claim 7, wherein said upper stratum displacement means comprises a plurality of activatable generally non-free-oxygen containing fluid jets disposed from the interior top area of the digesting chamber, whereby the spray of fluid from said jets displaces an upper stratum scum material from the digesting chamber into said output chamber for subsequent removal therefrom.

9. The anaerobic, displacement-type digester of claim 8, wherein said upper stratum displacement means further having said fluid jets tilted toward the output chamber, said fluid jets being operationally connected to a plurality of latitudinally extending fluid pipes disposed spacially from the interior top surface of said digester, said fluid pipes further being operationally connected to a fluid source outside said digester, and wherein said fluid pipes have means to be sequentially operable from the input end to the output chamber area of said digester.

10. The anaerobic, displacement-type digester of claim 7, wherein said output chamber additionally has ingress means for the removal of displaced materials therein, effluent output means disposed at the bottom thereof, gas output means disposed at the top area thereof, fluid input means for maintaining the sealing level between said partitions, and viewing means.

11. A method of removing an upper stratum scum layer from the digesting chamber of an anaerobic, displacement-type digester with minimal disturbance on the biological activity within the digesting chamber, said method comprising:
 (a) providing an anaerobic, displacement-type digester as provided by claim 7,
 (b) introducing organic waste materials into the input end of said digester,
 (c) allowing the stratification and biological transformation of the waste materials to take place within the digesting chamber of said digester,
 (d) transporting the upper stratum scum material from the digesting chamber to said output chamber by utilizing said upper stratum displacement means until a seal is formed between said partitions of said output chamber, and,
 (e) removing the displaced materials from said sealed output chamber.

* * * * *